United States Patent [19]

Rugheimer

[11] Patent Number: 4,827,921
[45] Date of Patent: May 9, 1989

[54] CONNECTING SYSTEM FOR GAS LINES FOR RESPIRATOR OR ANESTHESIA APPARATUS HAVING PLUGGABLE CONNECTING ELEMENTS

[76] Inventor: Erich Rugheimer, Maximilianplatz 1, D-8520 Erlangen, Fed. Rep. of Germany

[21] Appl. No.: 149,326

[22] Filed: Jan. 28, 1988

[30] Foreign Application Priority Data

Jan. 29, 1987 [DE] Fed. Rep. of Germany ....... 3702533

[51] Int. Cl.$^4$ .............................................. A62B 9/04
[52] U.S. Cl. .............................. 128/202.27; 128/912; 285/321; 604/283; 604/284
[58] Field of Search .......................... 128/202.27, 912; 604/283, 284; 285/317, 321

[56] References Cited

U.S. PATENT DOCUMENTS 4,557,261 12/1985 Rugheimer .

FOREIGN PATENT DOCUMENTS 732323 2/1943 Fed. Rep. of Germany .
1708014 4/1971 Fed. Rep. of Germany .

Primary Examiner—Edgar S. Burr
Assistant Examiner—Kimberly L. Asher
Attorney, Agent, or Firm—Browdy and Neimark

[57] ABSTRACT

A connecting system for gas lines for respirator or anesthesia apparatus comprising with at least two connecting elements which can be plugged into each other, a first connecting element comprising a Y-piece with an inhalation hose socket, exhalation hose socket and a connector extension piece, and a second connecting element comprising a second connector adapted to be connected with the connector extension piece, the second connector having a tube extension for an endotracheal tube, the first connecting element having at least one resilient securing element which resiliently engages under the force of a spring an annular groove in the outer wall of the second connecting element, and at least one manually operable unlocking element which temporarily overcomes the spring force of the securing element, the first and second connecting elements being freely rotatable in respect to each other. A resilient securing element and an unlocking element are moveably disposed within a peripheral wall area of one connecting element, for example a connector extension of a Y-piece of the connecting system, in such a way that the securing and unlocking elements do not extend beyond the periphery of the connecting elements either in the locked or the unlocked position.

22 Claims, 3 Drawing Sheets

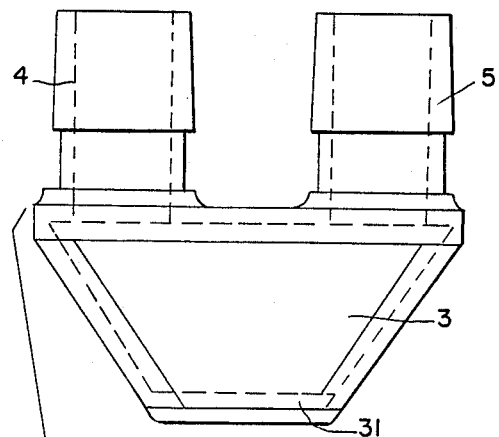
FIG. 1
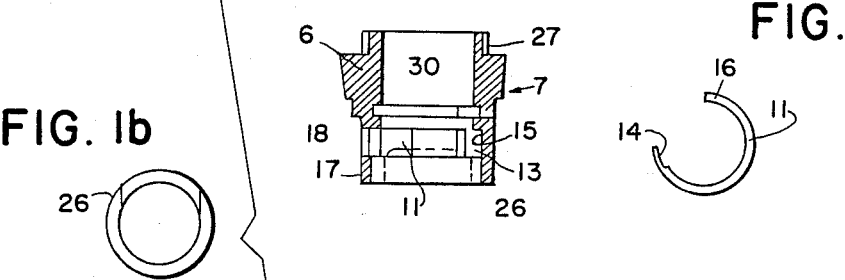
FIG. 1a
FIG. 1b
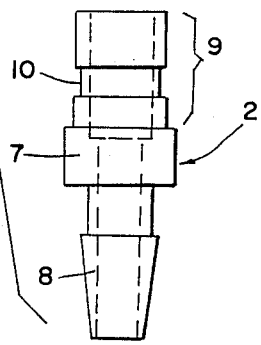
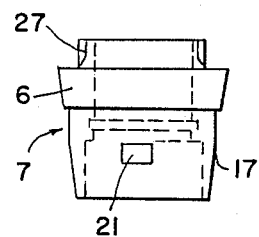
FIG. 2

FIG. 5
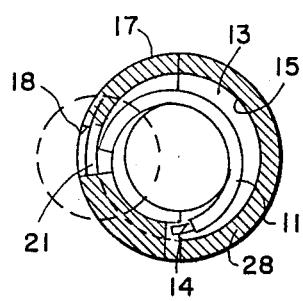
FIG. 6
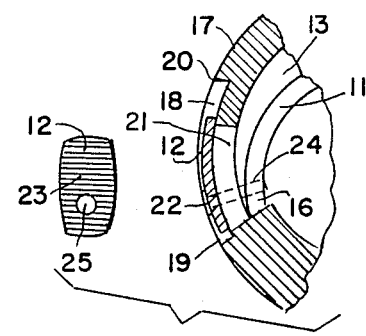
FIG. 3
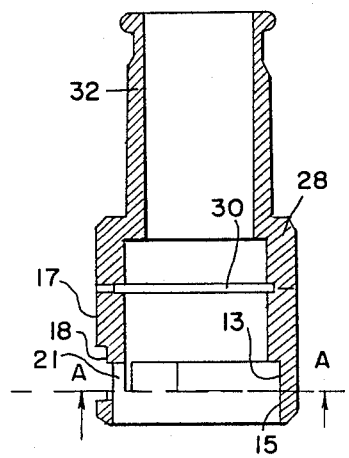
FIG. 4
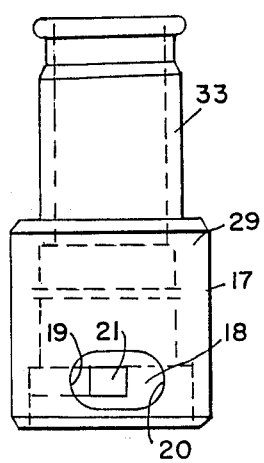
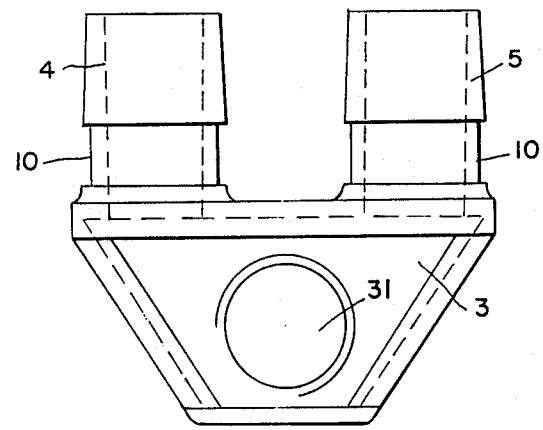
FIG. 7

CONNECTING SYSTEM FOR GAS LINES FOR RESPIRATOR OR ANESTHESIA APPARATUS HAVING PLUGGABLE CONNECTING ELEMENTS

BACKGROUND OF THE INVENTION

1. Field of the Invention

The invention relates to a connecting system for gas lines for a respirator or anesthesia apparatus with at least two connecting elements which can be plugged into each other.

2. The Prior Art

A connecting system is known in which the one connecting element has a securing element which resiliently engages an annular groove in the outer wall of another connecting element under the force of a spring, as well as a manually operable unlocking element which temporarily overcomes the spring action of the securing element. However, the arrangement of securing and unlocking elements, which radially extends beyond the periphery of the one connecting element, is troublesome and obstructive, particularly during the use of breathing masks prior to the insertion of tubes. By means of the novel connecting system it is intended that the use of breathing masks is no longer hampered and unwanted disconnection of the connected connecting elements becomes possible.

A connecting system is known from German Patent 3,048,223 which can be used during artificial respiration of patients with the aid of tubes, for example during anesthesia by means of an anesthesia apparatus before and during an operation, but also in the course of extensive artificial respiration of patients, for example in intensive care units. A breathing apparatus or an anesthesia apparatus is connected to a Y-shaped piece or a Y-piece via inhalation and exhalation tubes in the form of rubber or plastic tubes, the pipes or tubes being pushed onto an inhalation tube socket or an exhalation tube socket (legs of the Y-piece). The Y-piece has a connector extension onto which can be pushed a connector with a hose extension. An endotracheal tube, which is inserted into the trachea of a patient, is pushed onto the tube extension of the connector.

It is of importance that, if required, the connection between the Y-piece and the connector can be disengaged extremely fast in a simple manner with one hand, while during normal operation the connection is to remain rotatably movable such that the connector is rotatable within the connector extension. Additionally, it is also particularly important to avoid with the utmost assurance the unwanted and/or unrecognized disconnection of the plug connection between the connector extension and the connector, since there is the danger of lethal consequences if such disconnection is not detected at all or not in sufficient time and if, for this reason, artificial respiration of the patient is no longer performed correctly or even, not possible at all. Particularly for the purpose of, on the one hand, assuredly avoiding unwanted disconnection and, on the other, of performing desired and required disconnection in a simple manner with only one hand, during which no diminutions in the flow of the breathing air (or $O_2$) or the anesthetic gas (for example, nitrous oxide) are permitted to occur, it is further provided in the connecting system known from German Patent 3,048,223 to place at least one securing element in the form of a two-armed, unilaterally spring loaded-lever, which can be pivoted around a pin on the connector extension, transversely to its longitudinal axis, a spring element acting on the connector extension as well as on the outer lever arm prestressing the securing element in its locked position. A coil spring, for example, is used as the spring element and is disposed in an inner bore on the outer lever arm of the securing element and in an inner bore in the connector extension.

As a result, one connecting element, i.e., the connector extension, is automatically locked with the second connecting element, i.e., the connector, by axial insertion, while, by means of the unlocking element formed by the outer lever arm a desired disconnection of these two connecting elements is achieved.

Although experience during practical use of this known connecting system in hospitals has confirmed that the securing and disconnecting elements work flawlessly and in particular, partial or total disconnection can basically be avoided, it has been shown on the other hand that the disposition of the securing and unlocking elements, which radially extend beyond the periphery of the connector extension, has resulted in problems in a different area. These are, in particular that, because of their radial extension, the above-mentioned arrangement of the securing and unlocking elements is extremely troublesome when a patient, who is being given artificial respiration by means of a mask before being placed on the tube, has an endotracheal tube inserted into the trachea. It was attempted to circumvent these difficulties by the use of additional intermediate pieces of tubing, resulting in an increase of the axial length of the entire connecting system. However, these steps have proven to again be dangerous and troublesome because the respiration tubes connected to the Y-piece have exerted a much larger lever action on the throat area of the patient and further, because the anesthesiologist was unable to place the breathing mask on the face of the patient with sufficient precision, which led to the escape of air.

SUMMARY OF THE INVENTION

It is therefore an object of the present invention to provide a connecting system which overcomes the previously discussed problems and disadvantages, i.e., in which operation of the respirator masks is not hampered in any way while, at the same time, guaranteeing that unwanted disconnection of the connecting elements plugged into each other are avoided with certainty and desired and required disconnection can be performed in a simple manner with one hand.

At the same time it is intended to avoid leaks and to improve the operational ability of the entire system.

Based on a connecting system for gas lines for a respirator or anesthesia apparatus, this object is attained by the present invention by movably disposing the resilient securing element as well as the unlocking element within a peripheral wall area of the first connecting element in such a way that the securing and unlocking elements do not extend beyond the outer periphery of the respective connecting element either in their locked or in their unlocked position.

Advantageous further embodiments of the invention are contained in the dependent claims.

The fact that in the present connecting system no troublesome elements extend longer beyond the peripheral wall of the connecting element formed by the Y-piece with connector extension and the connector with tube extension, because the securing and unlocking elements extend at the same level as that of the outer wall, is of considerable importance in the invention. Because of this, problems with regard to a respirator mask and possible intermediate tubing pieces such as those described above will no longer occur in actual use.

Furthermore, the arrangement of the securing and unlocking elements according to the invention also makes it possible, for example, that these may be incorporated in multiple usable connecting elements, so that disposable parts no longer contain expensive components.

The invention relates to a connecting system which includes a Y-piece with an inhalation hose socket, exhalation hose socket and a connector extension forming the first of the connecting elements, and a second connector, which can be connected with the connector extension piece and which forms the second of the connecting elements and which has a tube extension for an endotracheal tube, the first connecting element having at least one resilient securing element which resiliently engages, under the force of a spring, an annular groove in the outer wall of the second connecting element, as well as at least one manually operable unlocking element which temporarily overcomes the spring force of the securing element, the connecting elements being freely rotatable in respect to each other.

BRIEF DESCRIPTION OF THE DRAWINGS

The following description of exemplary embodiments in connection with the drawings further describes the invention, its further characteristics and advantages; given only by way of example, and with reference to the accompanying drawings, in which:

FIG. 1 is a schematic side view of a connecting system, consisting mainly of a Y-piece, a first and a second connecting element, these components being shown in the unconnected position;

FIG. 1(a) is a schematic top view of a resilient securing element provided for the first connecting element in accordance with FIG. 1;

FIG. 1(b) is a schematic top view of an end ring for the first connecting element in accordance with FIG. 1;

FIG. 2 is a further schematic side view of the first connecting element in accordance with FIG. 1;

FIGS. 3 and 4 are, respectively, further exemplary embodiments of plug connector elements for a connecting system (in FIG. 3 in axial section, in FIG. 4 in a schematic side view);

FIG. 5 is a sectional view according to the plane A—A of FIG. 3;

FIG. 6 is a detail view in accordance with the circle in FIG. 5 with further components;

FIG. 7 is a further embodiment of a Y-piece for a connecting system in accordance with FIG. 1.

DETAILED DESCRIPTION OF THE PREFERRED EMBODIMENTS

Figure 8:
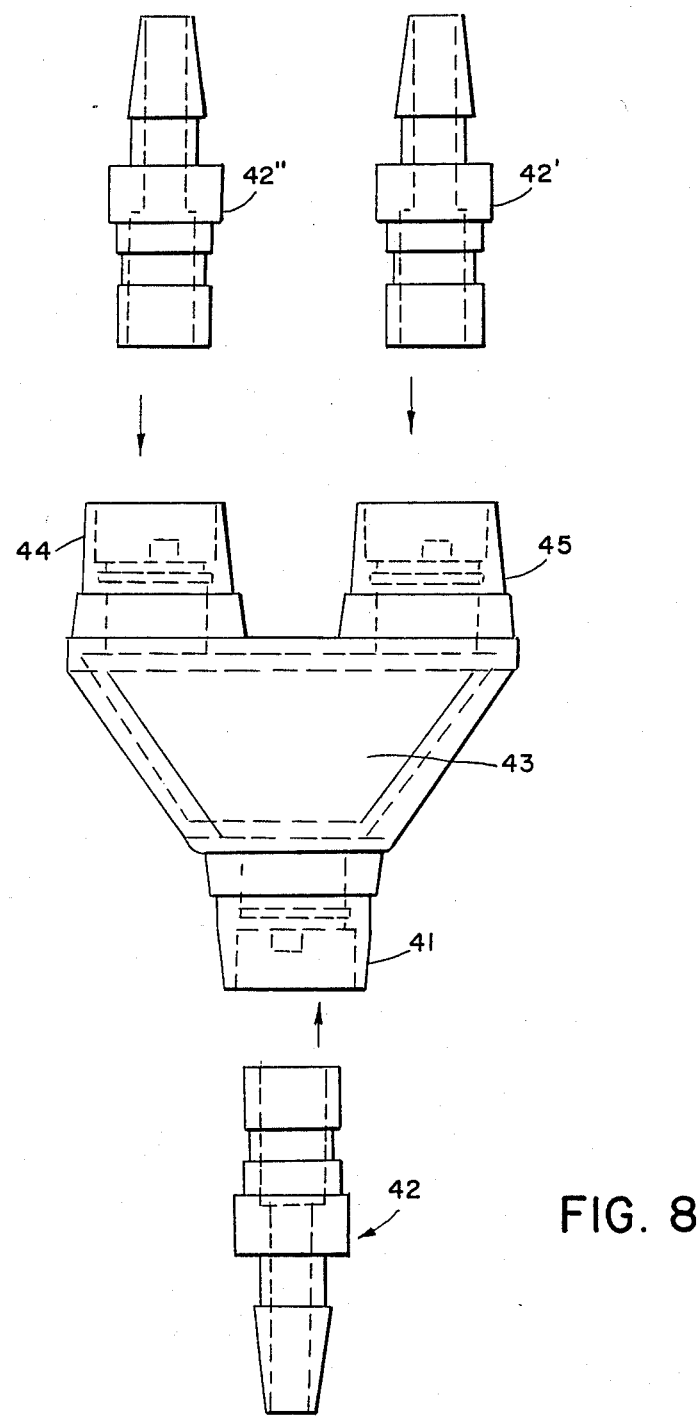
FIG. 8 is a schematic side view of a modified connecting system showing the individual components an un-connected condition.

A connection system is shown in FIG. 1 in an extended, partially sectional view, which mainly consists of a Y-shaped piece or a Y-piece 3, a first connecting element 1 as well as a second connecting element 2 which can be plugged into each other.

In the particular exemplary embodiment in accordance with FIG. 1, the first connecting element 1 is in the form of a connector extension 6 and the second connecting element 2 is in the form of a connector 7 with hose extension 8 which is used, for example, for the connection with an endotracheal tube (not shown). Also disposed on the Y-piece 3 are an inhalation tube socket 4 and an exhalation tube socket 5 to which can be connected breathing tubes (not shown) for connection with, for example, a respiration or an anesthesia apparatus.

The connector extension 6 has, in its plug connection area oriented away from the Y-piece, a securing element 11 and an unlocking element 12, details of which can be seen in FIG. 6.

The connector extension 6 is further provided with an outer thread 27 on its end area oriented away from the plug connection area, by means of which it can be screwed into a corresponding opening 31 in the opposite end of the Y-piece.

The securing element 11 and the unlocking element 12 are movably disposed inside the peripheral wall area of the connector extension 6 in such a way that the securing and unlocking elements do not extend beyond the outer periphery of the connector extension 6 either in the locked or in the unlocked position.

For this purpose a cut-out 13 in the form of a sector of an annular groove is provided in the inner wall 15 of the connector extension 6, while the securing element is formed as an autoresilient spring washer sector 11 (FIG. 1a). The spring washer sector 11 is preferably in the shape of an arc with an arc size of 3/2.

As shown more particularly in FIG. 5, the annular groove sector 13 is shaped mainly corresponding to the shape of the spring washer sector 11 or is adapted to this shape such that for attaining an unlocked position between the connector extension 6 and the connector 7, the spring washer sector 11 can be moved into the annular groove sector 13 when the unlocking element 12, which can temporarily overcome the spring action of the spring washer sector 11, is manually activated.

However, in the locked state, when the connector extension 6 and the connector 7 are axially pushed into each other, the spring washer sector 11 resiliently engages the peripheral annular groove 10 provided in the outer wall of the connector 7, the frontal area 9 of the connector 7, as a result of the plug connection made, being entirely inside the inner bore of the connector extension 6 until it touches its outer wall 17.

In detail, the spring washer sector 11 which is located inside the annular groove sector 13, is fixedly connected on its free end 14 with the inner wall 15 of the connector extension 6, while the spring washer sector 11 is fastened with its other free end 16 to the unlocking element 12 (see FIG. 6).

The spring washer sector 11 has an initial tension which defines the locked position.

In the present exemplary embodiment the spring washer sector 11 approximately corresponds to an arc extending over 270°, however, it is also conceivable that angles of the spring washer sector 11 different from this angle are possible.

Finally, the cut-out 13 in the form of an annular groove sector in the inner wall 15 of the connector extension 6 is outwardly limited in the plug connection area towards its end by an end ring 26 (also see FIG. 1(b)) which is inserted in a corresponding recess in the inner wall towards the end of the connector extension 6.

Furthermore, the outer wall 17 of the connector extension 6 has a cut-out 18 (also see FIG. 4) which is associated with the unlocking element 12. In detail, the unlocking element 12, which cooperates with the securing element 11, is movably supported within this cut-out 18 at a preset peripheral distance between the two end stops 19 and 20. The first end stop 19 corresponds to the locked position and the second end stop 20 corresponds to the unlocked position in regard to the first and second connecting element 1 and 2.

Furthermore, as shown in particular in FIGS. 3 and 5 which represent an exemplary embodiment of a plug connecting element 28 with a plug connector segment corresponding to the connector end 6, the cut-out in the inner wall 15 of the connecting element 28, which is in the form of the annular groove sector 13, is connected via an opening 21 in the wall of this connecting element with the cut-out 18, which receives the unlocking element 12, in the outer wall 17 of the connecting element 28.

Thus securing means 22 can be provided (see FIG. 6) which secure the unlocking element 12 through the opening 21 in the wall of the connecting element 28 with the corresponding free end 16 of the spring washer sector 11. As further shown in Fig. 6, the unlocking element 12 is in the form of a sliding disk, which is manually operable and can slide in the peripheral cut-out 18 associated with it. For easier operation this sliding disk has been provided with ribbing 23 on its outwardly oriented surface.

To provide a removable fastening between the unlocking element 12 and the spring washer sector 11, the free end 16 of the spring washer sector 11 intended for fastening with the unlocking element has a threaded bore 24 and the unlocking element 12 itself has a correspondingly disposed opening 25. The fastening means are in the form of a screw 22 by means of which the unlocking element or the sliding disk 12 can be secured with the spring washer sector 11 in the area of the peripheral opening 21 of the outer wall 17 of the connecting element 28.

A manual sliding of the unlocking element 12 from its first end stop 19 to its second end stop 20 results in the temporary cancellation of the initial tension of the spring washer sector 11 which defines the locked position. The spring washer sector 11 moves entirely into the cut-out in the form of an annular groove sector 13. In this way the state of unlocking of the connecting elements which had been plugged into each other has been reached, and persists until the unlocking element 12 is released again. This then again moves on its own under the spring force of the spring washer sector into its opposite end stop position within the cut-out 18. The spring washer sector 11 moves on its own into the locking position in which it narrows the cross section of the inner wall 15 of the plug connecting element 1 or 28, as shown in FIG. 5, so that area of the spring washer sector 11 drawn out of the annular groove sector 13 into the cross section engages the annular groove 10 in the outer wall of the other connecting element 2 or 4.

As also shown in FIG. 7, the Y-piece can also be formed in such a way that the connector extension 6 in accordance with FIG. 1 can be attached in a vertical direction such that the axis of the connector extension forms a right angle with the axis of the Y-piece. Therefore the thread opening 31 is located in the side wall of the Y-piece 3.

Furthermore FIG. 7 shows (the same way as FIG. 1) that the inhalation tube socket 4 and the exhalation tube socket 5 respectively form third and fourth plug connector elements with plug connectors at their ends which are formed corresponding to the plug connector area 9 of the connector 7 and have an outer annular groove 10. Because of this, these plug connector elements 4 and 5 can be used in the same way with the plug connector elements 28 according to FIG. 3 and 29 according to FIG. 4 as has already been described by means of FIG. 1 for the connection between the connector extension and connector 7.

Furthermore, the plug connector elements 28 and 29 also have hose extensions 32 and 33 which are used for connection with the respective respiration hoses.

The form of the hose extensions 32 and 33 could also be such that they, in general, correspond to the form of the tube extension 8 of the connector 7 according to FIG. 1.

Finally, as shown in FIGS. 1, 3 and 4, the plug connector elements 6, 28 and 29 respectively have an 0-ring seal 30 in the inner wall area following the securing and unlocking elements 11 and 12, which also presents substantial advantages with respect to the reusability of these components.

These O-ring seals 30 are used for mutual sealing when the connector extension 6 is plugged together with the connector 7 or the plug connector elements 28 and 29 with the hose extensions 4 and 5.

The connecting system shown in FIG. 8 is modified with respect to the one shown in FIG. 1 in that the inhalation tube extensions and the exhalation tube extensions 4, and 5 have been replaced by tube extensions 44, and 45. Tube extension connectors 42' and 42" are inserted into tube extensions 44 and 45, and can be locked into position therein. As a result, the structure of the system shown in FIG. 1 is simplified, which in particular decreased the cost of manufacturing the system.

A detailed description of the embodiment according to FIG. 8 is not required, since the system components 41 and 42 or 44, 45, 42' and 42" completely correspond to the components 1 and 2 in FIG. 1.

The components of the connecting system according to the invention described above can also be entirely or partially made of plastic.

It is understood that the exemplary embodiments described above are shown by way of example only and that further variations and improvements are possible within the scope of the invention.

What is claimed is:

1. A connecting system for gas lines for respirator or anesthesia apparatus comprising:
   at least two connecting elements which can be plugged into each other;
   a first connecting element comprising a Y-piece with an inhalation hose socket, exhalation hose socket and a connector extension piece; and
   a second connecting element comprising a second connector adapted to be connected with the connector extension piece, said second connector having a tube extension for an endotracheal tube, the first connecting element having at least one resilient securing element which resiliently engages under the force of a spring an annular groove in the outer wall of the second connecting element, and at least one manually operable unlocking element which temporarily overcomes the spring force of said securing element, said first and second connecting elements being freely rotatable with respect to each other, said resilient securing element and said unlocking element being movably disposed within a peripheral wall area of said first connecting element in such a way that said securing and unlocking elements do not extend beyond the outer periphery of said first connecting element either in the locked or the unlocked position.

2. A connecting system in accordance with claim 1, wherein said securing element comprises an auto-resilient spring washer sector.

3. A connecting system in accordance with claim 2, further comprising a first cut-out, corresponding to the spring washer sector, in the form of an annular groove sector provided in the inner wall of said first connecting element and wherein the spring washer sector is movable into said cut-out for the purpose of attaining the unlocked position.

4. A connecting system in accordance with claim 2, wherein the spring washer sector is fixedly fastened at one free end to an inner wall of said first connecting element and is fastened to the unlocking element at a second free end.

5. A connecting element in accordance with claim 2, wherein the spring washer sector has an initial tension which defines the locked position.

6. A connecting system in accordance with claim 3, wherein the unlocking element is movably supported within an associated second cut-out in an outer wall of said first connecting element at a preset peripheral distance between two end stops, the first end stop corresponding to the locked position and the second end stop corresponding to the unlocked position.

7. A connecting system in accordance with claim 6, wherein the cut-out in the form of an annular groove sector in the inner wall of said first connecting element is connected via an opening in the wall of said first connecting element with the second cut-out, receiving the unlocking element, in the outer wall of said first connecting element.

8. A connecting system in accordance with claim 7, further comprising fastening means provided for fastening the unlocking element through the opening in the wall of said first connecting element with a corresponding free end of the spring washer sector.

9. A connecting system in accordance with claim 8, wherein the fastening of the unlocking element with the spring washer sector can be released.

10. A connecting system in accordance with claim 8, wherein the unlocking element comprising a sliding disk, which is slidable in the associated peripheral second cut-out in the outer wall of said first connecting element.

11. A connecting system in accordance with claim 10, wherein the sliding disk is provided with ribbing on its outwardly oriented surface.

12. A connecting system in accordance with claim 9, wherein the free end of the spring washer sector intended for fastening to the unlocking element has a threaded bore and the unlocking element itself has a correspondingly placed opening, said fastening means comprising a screw by means of which the unlocking element can be fastened with the spring washer sector in the area of the peripheral opening of the wall of said first connecting element.

13. A connecting system in accordance with claim 12, wherein the cut-out in the form of an annular groove sector in the inner wall of said first connecting element is outwardly limited in the plug connection area towards its end by an end ring which is insertable into a corresponding recess in the inner wall towards the end of the connecting element.

14. A connecting system in accordance with claim 13, further comprising a fastening pin for securing the one free end of the spring washer sector to the inner wall of the one connecting element, axis-parallel insertion bores corresponding to said fastening pin being provided in the end of the respective spring washer sector and in the end wall area of said first connecting element in the area of the end of the respective annular groove sector.

15. A connecting system in accordance with claim 14, wherein said fastening pin is used for fastening an end ring which has a respective axis-parallel insertion bore for receiving said fastening pin.

16. A connecting system in accordance with claim 15, wherein said fastening pin comprises a metal pin, in particular a steel pin.

17. A connecting system in accordance with one of claim 2, wherein the spring washer sector used as securing element is made of plastic-clad metal, in particular steel.

18. A connecting system in accordance with claim 2, wherein the spring washer sector used as securing element is made of plastic only.

19. A connecting system in accordance with claim 2, wherein the spring washer sector is in the shape of an arc with an arc size of 3/2.

20. A connecting system in accordance with claim 2, wherein said connector extension of the Y-piece, forming the first connecting element, has on its end area oriented away from the plug connector area containing the securing and unlocking elements, a thread for making a threaded connection with the Y-piece.

21. A connecting system in accordance with claim 20, wherein the inhalation hose socket and the exhalation hose socket of the Y-piece respectively comprise third and fourth plug connecting elements having plug connecting segments at their ends which are formed corresponding to the plug connecting segment of said first connecting element and in that fifth and sixth plug connecting elements are provided as tube extensions, the respective plug connection segments at their ends are formed corresponding to the plug connection segment of said connector extension.

22. A connecting system in accordance with claim 21, wherein said connector extension piece and the fifth and sixth connecting elements respectively have an O-ring seal in an inner wall area following the securing and unlocking elements.

* * * * *